United States Patent [19]

Jha et al.

[11] Patent Number: 5,032,265

[45] Date of Patent: Jul. 16, 1991

[54] METHOD AND SYSTEM FOR PRODUCING STERILE AQUEOUS SOLUTIONS

[75] Inventors: Anil D. Jha, Lexington; Laura L. Deming, Lunenburg; Ralf Kuriyel, Boston, all of Mass.

[73] Assignee: Millipore Corporation, Bedford, Mass.

[21] Appl. No.: 541,010

[22] Filed: Jun. 20, 1990

[51] Int. Cl.⁵ .............................................. B01D 61/08
[52] U.S. Cl. .............................. 210/195.2; 210/257.2; 210/321.69
[58] Field of Search ............... 210/637, 634, 638, 644, 210/649–652, 679, 195.2, 257.2, 175, 321.64, 321.69, 321.72, 500.21

[56] References Cited

U.S. PATENT DOCUMENTS 4,808,287 2/1989 Hark .................................... 210/637

Primary Examiner—Frank Sever
Attorney, Agent, or Firm—Andrew T. Karnakis; Paul J. Cook

[57] ABSTRACT

A process is provided for purifying potable water to produce American Association for Advancement of Medical Instrumentation (AAMI) standard water for dialysis, United States Pharmacopeia Convention, Inc. USP XXII specifications water for injection or sterile water for injection. Potable water is passed through a plurality of treatment steps including a preliminary filtration step, a carbon adsorption module and a reverse osmosis module to produce water to the quality specified by AAMI for hemodialysis. An ion exchange filtration step is added to the steps stated above to produce USP XXII quality specifications for water for injection and a disposable sterilizing microfilter is further added to all the steps stated above to produce sterile water for injection. The process is designed such that the system is sanitized with hot water and subsequently flushed at a temperature and time that will control microbial population as specified by the user requirements without degrading the materials of construction in the treatment steps, for example at 80° C. for one hour. The sterile microfilter used for the production of sterile water is a disposable device changed periodically to maintain sterility of the final solution.

15 Claims, 5 Drawing Sheets

1

METHOD AND SYSTEM FOR PRODUCING STERILE AQUEOUS SOLUTIONS

BACKGROUND OF THE INVENTION

This invention relates to a method and system for producing purified water, sterile water or a sterile aqueous solution for biological and medical uses. More particularly, this invention relates to a method and apparatus for producing sterile aqueous solutions meeting all user specifications including bacteriological specifications to permit their administration directly or indirectly to a patient.

Conventional water purification systems employing well known technologies such as reverse osmosis, deionization and ultrafiltration are capable of producing chemically and biologically pure water for short periods of time. Generally, when these systems are operated continuously, they will maintain low levels of bacteria and pyrogens for a time period which is dependent upon the temperature at which the system is operated. During system operation, biologically active materials such as bacteria, yeast, mold and pyrogens will begin to proliferate within the system to unacceptably high amounts leading to biological contamination of the normally pure water produced by these systems.

Some conventional systems regain their capacity to produce biologically pure water by rinsing of the systems with sanitizing agents such as formalin or chlorine which control biologic contaminants. While these sanitizing agents perform their function well, they are highly toxic to humans, are difficult to handle and are difficult to rinse out of the purification system. The use of these chemicals has major adverse environmental impact as well.

A second method for insuring biologic purity of water treated with a membrane filter system is to treat the system with a second process which insures the control of all living organisms. One such method is to heat the water with a pasteurization process. However, components within the system such as certain reverse osmosis membranes cannot withstand pasturization temperatures. Therefore, when utilizing a system which is sanitized with high temperature water, undesirable by-pass loops and valves to reverse osmosis units are introduced. Therefore, this method does not clean and sanitize the reverse osmosis unit.

A third method is to pass the purified water through a filter that is capable of filtering from the water all biologically active material. However, this process requires that the initial filtration treatment reduces the bacterial contamination to sufficiently low levels so that the bacterial removal filter does not clog prematurely. This is a very expensive proposition which renders it impractical. Therefore after initial filtration, chemical sanitization agents are still currently required to maintain low bacterial levels in the system.

It has been proposed in U.S. Pat. No. 3,578,774 to provide sterile urological irrigating liquid composition by passing the fluids continuously through a filter designed for removing bacteria. However, this device requires an on site source of nonpyrogenic water and urological fluid. It has also been proposed in U.S. Pat. No. 4,253,457 to prepare such irrigation solutions on site by utilizing a combination of a reverse osmosis unit for removing pyrogens, a deionization unit for removing dissolved solids and pyrogens and a filter for removing bacteria in order to produce pyrogen free, bacteria free solution that can be administered directly to the patient. However, this system is limited since the claim of removing pyrogens by deionization is limited to removal of some pyrogens, but not all, as required for production of bacteria and pyrogen free water. In addition, the system requires chemical sanitization and cleaning; thereby increasing risk to the patient. Neither of the means disclosed in U.S. Pat. Nos. 3,578,774 or 4,253,457 are capable of producing water that meets the USP XXII standards for water for injection or for irrigation for long periods without continuous monitoring, caring and chemical sanitization of the unit by an operator.

British Patent Nos. 1,450,030 and 2,034,584 also disclose means for providing pyrogen free and bacteria free aqueous solution at the site of use of the solutions. However, each of these systems relies upon the use of chemical disinfectant such as with formalin to sanitize the equipment or flash sterilization wherein the water used to form the aqueous solution is heated to a temperature, typically 150° C. to 160° C. The use of chemical sanitization is undesirable even though it is an effective means for killing microorganisms because it also introduces harmful chemicals into the system which can be administered accidentally to the patient. Furthermore, heat sterilization of the water used to form the aqueous solution is undesirable since sterilization is accomplished only in portions of the system exposed to the high temperature. The bacteria and pyrogens continue to multiply in the remaining portion of the system thereby preventing the desired fluid quality from being produced.

U.S. Patent No. 4,610,790 discloses a system for forming USP XX grade water from tap water which includes a carbon-based filtration unit, a reverse osmosis unit, a deionization unit and an ultrafiltration unit. In order to cleanse the system of accumulated microorganisms and pyrogens, the ultrafiltration unit and the deionization unit are flushed with heated water. The reverse osmosis unit is flushed with unheated water and the carbon-based filtration unit is replaced periodically. Since the carbon-based filtration unit and reverse osmosis unit are not exposed to heated water, additional bypass loops and valves must be added to the system. The non-sanitized filter units may eventually produce unacceptable quality product. Furthermore, this system requires a redundant filtration unit for removal of bacteria and pyrogens because the reverse osmosis unit can not be heat sanitized.

Accordingly, it would be desirable to provide a means for producing sterile water which requires minimal care and maintenance, automatically sanitizes and monitors system performance and eliminates chemical sanitization, by-pass loops and redundant filtration steps.

SUMMARY OF THE INVENTION

In accordance with this invention, a method and system are provided for producing water quality that meets AAMI water for dialysis standards, USP XXII water for injection and sterile water for injection specifications. Potable water is passed through a preliminary filtration step, a carbon adsorption module and a reverse osmosis module to produce water quality that meets the AAMI water standard for dialysis. To produce water quality that meets the USP XXII water for injection, an ion exchange filtration step is added to the system, if necessary, that produces AAMI water from water containing undesirably high salt concentration. In order to produce sterile water for injection, a disposable sterile microfilter is added as a final element for producing USP XXII grade water.

The system can be utilized to produce solutions such as peritoneal dialysis fluid, intravenous injection fluid and other medical use fluids. The fluid production is accomplished by accurately metering a concentrated fluid into the high purity water produced by the system at a given ratio, e.g., a sodium chloride injection concentrate (twenty times concentrated) is mixed with USP XXII grade water for injection at the rate of nineteen parts water to one part concentrate and then passed through a disposable sterile microfilter to produce sterile sodium chloride injection solution. The final solution can either be packaged in sterile intraveneous (IV) containers or used directly in medical applications. Similarly, peritoneal dialysis fluids can be produced by addition of concentrated peritoneal dialysis fluid to the AAMI standard water produced by the system and then passing the solution through a disposable sterile microfilter. The final solution can either be packaged in sterile containers or administered directly into the abdominal cavity of the patient.

The microbiological control in all of the systems described above is accomplished by periodic recirculation and/or flushing of high temperature water for a given period of time over all permanent wetted surfaces within the system including the preliminary filter, the carbon adsorption module, the reverse osmosis module and the ion exchange filtration module but excluding items that are replaced periodically such as the disposable sterile microfilter. If a semi-permanent sterile microfilter, such as ceramic microfilter, is utilized it can also be sanitized during the sanitization phase.

DESCRIPTION OF SPECIFIC EMBODIMENTS

Figure 1:
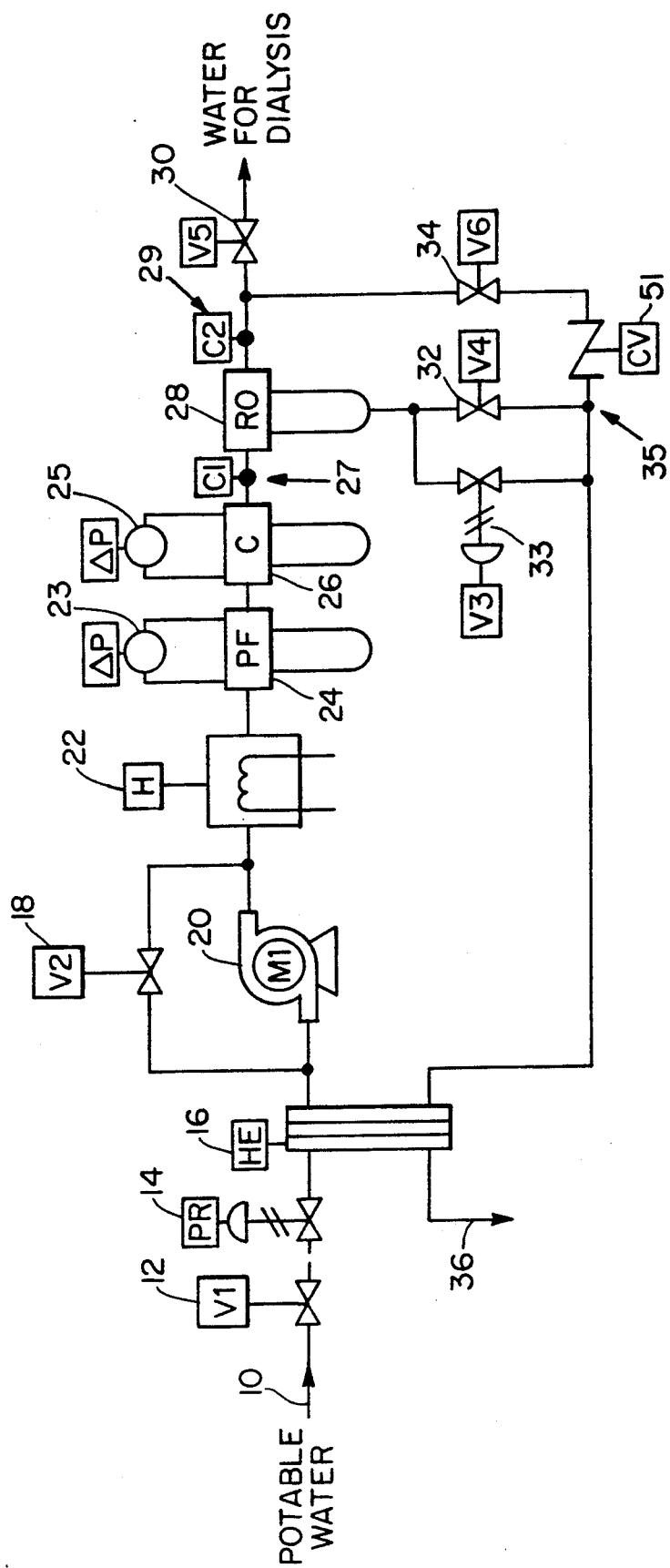
FIG. 1 is a schematic diagram of the method and system of this invention for producing water which meets specifications of AAMI standard water for dialysis.

In accordance with this invention, USP XXII grade sterile water for injection is produced by subjecting potable water to prefiltration, carbon adsorption, reverse osmosis, deionization and finally sterile microfiltration. The USP XXII specifications for water injection are detailed in The United States Pharmacopeia Convention, Inc, XXII pages 1456 and 1457 dated Jan. 1, 1990. The specifications include allowable limits on heavy metals and other chemical (organic and inorganic) contaminants, pH and total dissolved solids. The purified water must be sterile and non-pyrogenic.

The chemical impurities in the potable water are removed by the various filtration methods incorporated in the system. The prefilter element removes particulate matter present in the water. The carbon filter element satisfies the dual requirement of removing halogens as well as dissolved organics present in the incoming water. The reverse osmosis element removes dissolved ionic impurities, certain organics and is also a barrier for bacteria and pyrogens present in the water. The deionization element removes remaining trace ionic impurities in the purified water from the reverse osmosis module. Finally, the sterile microfilter is a sterile barrier for any remaining bacteria in the system.

To maintain a sanitary system, i.e., control of the bacteria population and pyrogen level within the system, a novel method of periodic system sanitization, preferably daily, is employed. The sanitization is accomplished by circulating or flushing hot water through the system for a time temperature combination sufficient to effect system sanitization, but less than that at which degradation of material in a module occurs. For example, water at a temperature of about 80° C. to 100° C., can be circulated through the system for up to two hours. The heated water is passed over all wetted surfaces in the system thereby limiting any bacteria growth during system operation and/or idle period. The pyrogens generated during system operation, idle period and during sanitization are flushed away in the post sanitization flush of the system. During the operating period, the reverse osmosis module continues as a barrier for bacteria and pyrogens. At the end of the operating period (during sanitization) the heated water kills the bacteria on the inlet side of the reverse osmosis module as well as any bacteria that may have passed through the reverse osmosis module. The pyrogens are flushed away during the post sanitization flush from all sections of the system. The disposable sterile microfilter is a barrier for any bacteria in the system and is always employed during operation but is disposed of prior to sanitization. The microfilter is changed periodically and therefore does not require sanitization. Certain microfilters such as ceramic microfilters may be semi-permanent and therefore may be sanitized along with other components.

The ability of the system to produce sterile water for injection is dependent on a combination of three major operating modes. They are: (1) Production of sterile water for injection (2) System sanitization and (3) System flush. A typical operating method for operating the system comprises the production of sterile water for approximately twenty-two hours. Thereafter, the system is sanitized with heated water, such as at 80° C. for two hours, followed by a system flush with cool water for about fifteen (15) minutes. After flushing, the system is ready to produce sterile water again in accordance with the described method.

During the water production phase, the filters remove impurities as described above from the incoming potable water. The prefilter element, carbon element and deionization element retain their respective impurities and at exhaustion of capacity, they are discarded. The reverse osmosis element is a tangential flow device consisting of three separate streams; namely, feed, reject and product. The water from the feed side sweeps across the surface of a semi-permeable membrane in the element and is discarded via the reject stream. A portion of the feed water passes through the membrane as purified water for further processing if necessary. The microbial impurities from the feed water are retained and/or discarded via the reject stream.

A very minute quantity of microbiological contaminate may pass through the reverse osmosis element and contaminate the elements positioned downstream of the reverse osmosis element. These contaminants are then captured by the disposable sterile filter element located downstream. By this means, sterile water can be produced by the system.

It is a well established fact that bacteria when left uncontrolled in a water system will proliferate and eventually produce water quality below the desired specifications for microbiological contaminants. To manage the bacteriological population within the system an innovative method is developed. The method involves sanitization of the total system at a temperature and time that will control microbial population to the desired level as required by the user requirements, for example, approximately 80° C. or higher temperature for approximately two hours on a daily basis. The recirculation and/or flushing of heated water through the system controls the bacteria present in the prefilter element, the carbon element, the inlet and outlet sides of the reverse osmosis element and any associated piping and accessories in the fluid path. Upon completion of the sanitization period, the system is flushed to carry away the destroyed bacteria and the fluid production can resume. By utilizing this periodic heat sanitization, any biofilm which has been formed within the system is inactivated since the destructive heat penetrates the entire thickness of biofilm formed. This is in contrast to chemical sanitization which generally is not as effective in controlling biofilms.

Referring to FIG. 1, the system utilized in the present invention includes a water inlet 10 for potable tap water which is controlled by valve (V1) 12 and pressure regulator (PR) 14. A heat exchanger (HE) 16 is provided to recover wasted heat exiting from the system. The tap water is pumped by means of pump (M1) 20. A bypass valve (V2) 18 is utilized for feed flow rate control to the reverse osmosis element. The tap water is directed to heater (H) 22, which may be activated to maintain a desired operating temperature of the system. The water is then passed through prefilter (PF) 24 and prefilter 24 is provided with differential pressure monitors ($\Delta P$) 23 which determine when the pressure across the prefilter exceeds a predetermined limit for filter changeout. The water is then passed through an adsorption element (C) 26 containing temperature resistant ion exchange resin, activated carbon particles or mixtures thereof, the adsorption particles utilized in step 26 are capable of withstanding the heat of the water utilized to sanitize the system in a subsequent sanitization step. Differential pressure monitors ($\Delta P$) 25 may be used to determine when the pressure across the element exceeds a predetermined standard pressure for change out. The filtered water then is passed to reverse osmosis unit (RO) 28 containing a temperature resistant membrane capable of withstanding the heat of the water utilized in the subsequent sanitization step. Conductivity monitors (C1), (C2), 27 and 29 monitor the performance of the reverse osmosis unit (RO) 28. Conductivity monitor (C2) 29 also assures the quality of the water produced. The reject conduit from reverse osmosis unit (RO) 28 passes through back pressure regulator V3 (33) which allows for adjustment of the product to reject ratio. Valve (V4) 32 remains closed during operation and is left open during sanitization since minimal back pressure is desired for the operation of the reverse osmosis unit (RO) 28 at high sanitization temperatures. During normal operation, the purified water is passed through valve (V5) 30 and then to be used as water for dialysis. Valve (V6) 34 remains closed during normal operation. When the system is sanitized with water heated by heater (H) 22, it passes through prefilter (PF) 24, adsorption unit (C) 26, reverse osmosis unit (RO) 28 and then splits to valve (V4) 32 on reject conduit side and valve (V6) 34 on product side while valve (V5) 30 remains closed during sanitization. The water from reject conduit side and valve (V6) 34 are combined at location 35 and passed through heat exchanger (HE) 16 to recover heat prior to passing to drain 36. The heater (H) 22 then is deactivated at the completion of sanitization and the system is flushed of the heated water by means of incoming potable water. An air break or a check valve (CV) 51 is included in the drain line to prevent any backflow of contaminated water into the product.

Figure 2:
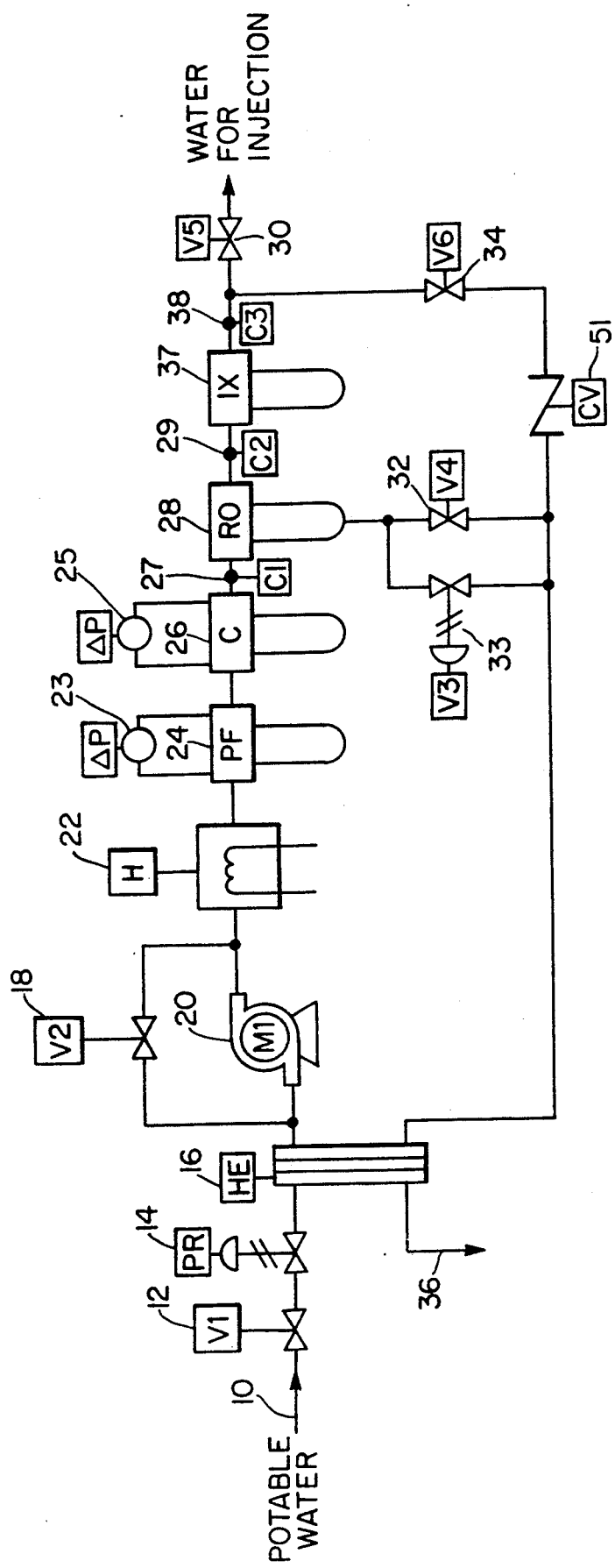
FIG. 2 is a schematic diagram of the method and system of this invention for producing water quality that meets USP XXII specifications for water for injection quality water.

Referring to FIG. 2, the elements of FIG. 1 are included in the system of FIG. 2 and are labeled with the same reference numerals. The system of FIG. 2 includes an ion exchange module (IX) 37 if necessary, in order to render the system capable of producing water quality equivalent to or better then standards specified in USP XXII water for injection from water feed containing undesirably high salt concentration. Conductivity monitors (C2) and (C3), 29 and 38, monitor the efficiency of the ion exchange module (IX) 37. Conductivity monitor (C3) 38 also assures the quality of water produced. When sanitizing the system with hot water, the heater (H) 22 is activated as water passes through the reverse osmosis unit (RO) 28 as discussed in FIG. 1. The water from the product side of the reverse osmosis unit (RO) 28 passes through the ion exchange module (IX) 37 and then through valve (V6) 34, combines with water from valve (V4) 32 and then is discarded via heat exchanger (HE) 16 through drain 36. Valve (V5) 30 remains closed during sanitization. The system then is flushed in the manner set forth above.

Figure 3:
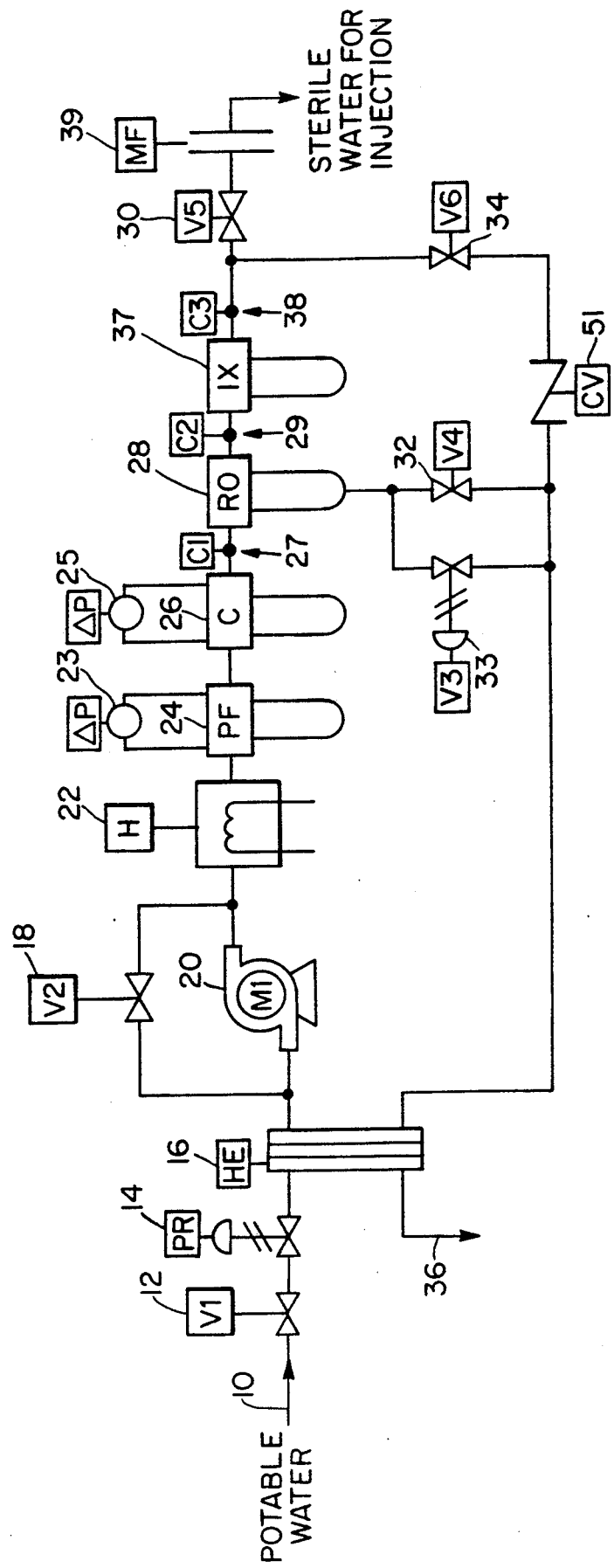
FIG. 3 is a schematic diagram of the method and system of this invention including a sterile microfilter for producing water quality that meets USP XXII specifications for sterile water for injection quality water.

Referring to FIG. 3, the elements of FIG. 2 are included in the system of FIG. 3 and are labeled with the same reference numerals. The system of FIG. 3 includes a sterile microfilter (MF) 39 which is disposed of after a cycle of producing sterile water for injection. During the sanitization step, heater 22 is activated and hot water is circulated through the modules 24, 26, 28 and 37 and then through 34 to 16 to drain 36. Thereafter, the system is flushed out with water to elute the remaining pyrogens which are directed to drain 36.

Figure 4:
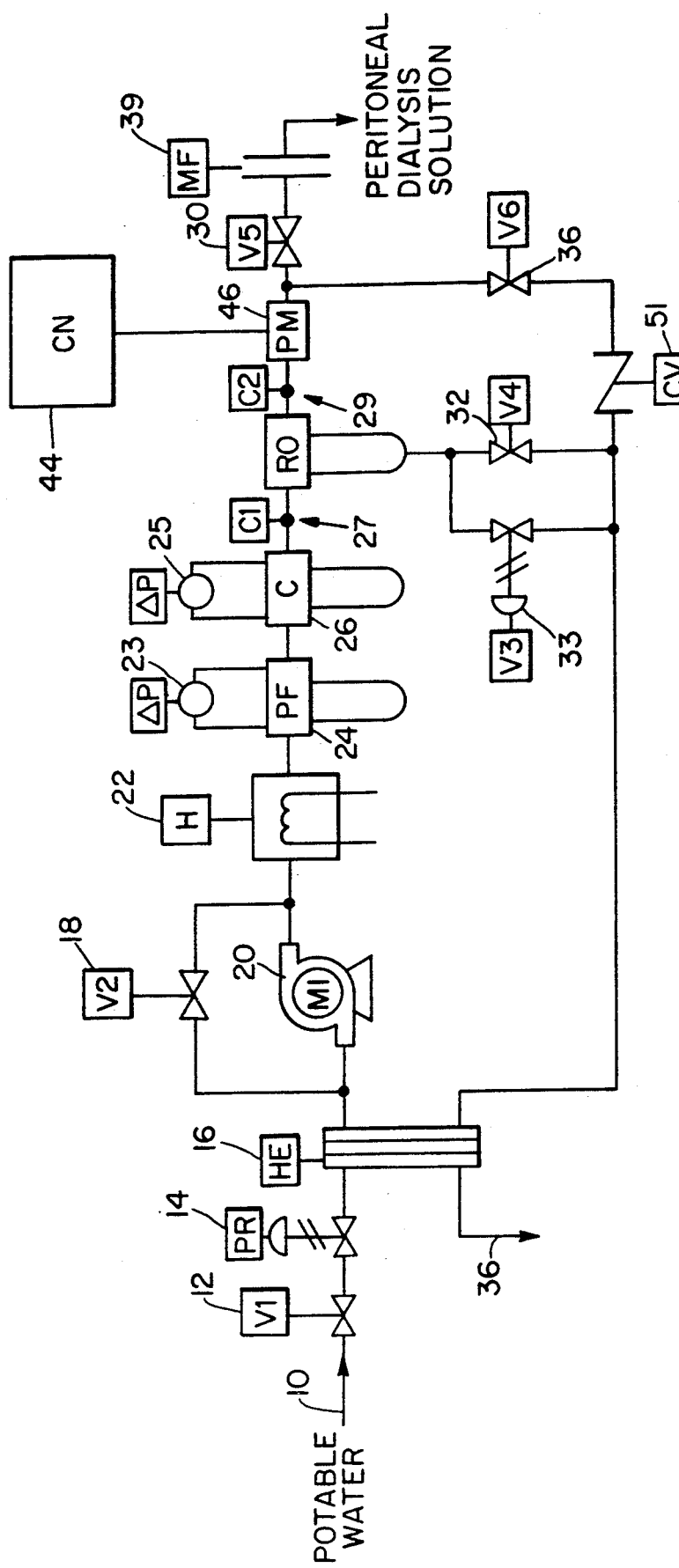
FIG. 4 is a schematic diagram of the method and system of this invention for producing sterile peritoneal dialysis solution.

Referring to FIG. 4, a system is shown for producing a solution containing a medicament such as peritoneal dialysis solution. The system shown in FIG. 4 is identical to the system shown in FIG. 1 except that means for proportioning purified water and a concentrated medicament is provided. All of the other components function in the manner described above. A concentrated peritoneal dialysis (medicament) solution is stored in container 44 and is dispensed via proportioning module 46 into admixture with the purified water from the reverse osmosis module (RO) 28. Thereafter, the proportioned solution is passed through sterile microfilter (MF) 39 for use. The sanitization of the system is the same as shown in FIG. 1 but, if desired, the container (CN) 44 and associated piping can be included in the high temperature sanitization loop to maintain control of bacteria and pyrogens. The system then is flushed in the manner set forth above.

Figure 5:
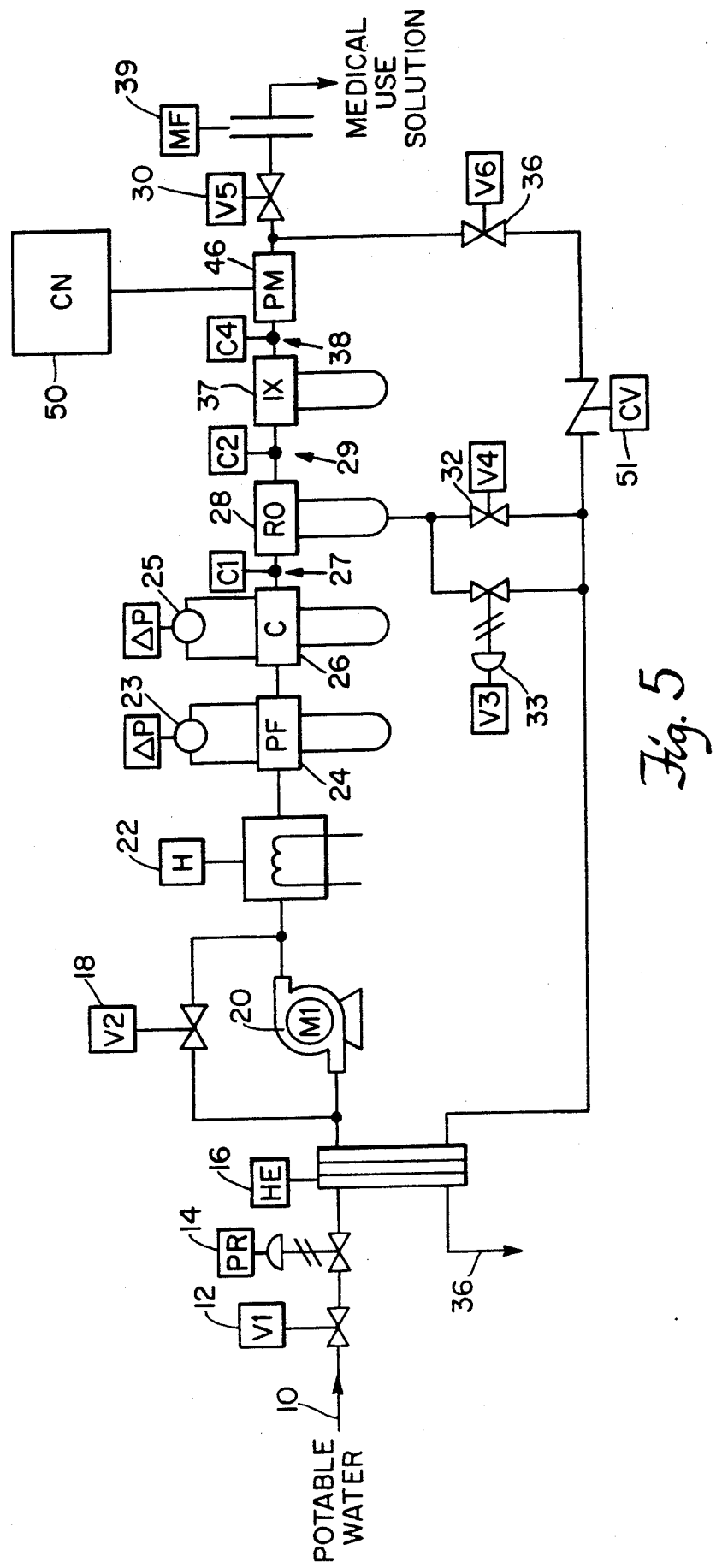
FIG. 5 is a schematic diagram of the method and system of this invention for producing a sterile medical solution.

Referring to FIG. 5, the elements of FIG. 4 are included in the system which function in the manner described above with the addition of an ion exchange module (IX) 37. The concentrated medical solution is stored in container (CN) 50, is dispensed via proportioning module 46 into admixture with the purified water from ion exchange module (IX) 37. The resulting dilute medical solution is passed through sterile microfilter 39 for use. The sanitization of the system is the same as shown in FIG. 2 but, if desired, the container (CN) 50 and associated piping can be included in the high temperature sanitization loop to maintain control of bacteria and pyrogens. The system then is flushed in the manner set forth above.

It is to be understood that the above description of the Figures describes the preferred embodiments of this invention. The adsorption step (C) 26 and reverse osmosis step (RO) 28 can be in any sequence. For example, if the incoming impure water contains no chlorine or if the reverse osmosis membrane is chlorine resistant, reverse osmosis step (RO) 28 can precede adsorption step (C) 26. However, the sterilizing microfilter (MF) 39 is always utilized downstream of the reverse osmosis and/or adsorption steps when producing sterile product.

We claim:

1. A system for producing water of a quality that meets AAMI Standard water for dialysis from a potable water source which comprises:
   (a) a filtration means adapted to remove particulate impurities from water;
   (b) an adsorption means containing an adsorbent for removing chlorine and dissolved organics;
   (c) a reverse osmosis separation means adapted to remove organics, dissolved solids, microorganisms and pyrogens from water;
   (d) means for passing the potable water through said filtration means, adsorption means and said reverse osmosis separation means and;
   (e) means for passing heated water periodically through said filtration means, said adsorption means and said reverse osmosis means thereby to flush accumulated pyrogens and to control microorganisms within the said system.

2. A system of claim 1 wherein the potable water is passed, sequentially through steps (a), (b) and (c).

3. A system for producing USP XXII specifications grade water for injection from a potable water which comprises:
   (a) a filtration means adapted to remove particulate impurities from water;
   (b) an adsorption means containing an adsorbent for removing chlorine and dissolved organics;
   (c) a reverse osmosis separation means adapted to remove organics, dissolved solids, microorganisms and pyrogens from water;
   (d) means for passing the potable water through said filtration means, said adsorption means, said reverse osmosis means and said deionization means; and
   (e) means for passing heated water periodically through said filtration means, said adsorption means said reverse osmosis means and said deionization means thereby to flush accumulated pyrogens and to control microorganisms within the said system.

4. The system of claim 3 wherein the potable water is passed sequentially through steps (a), (b) and (c).

5. A system for producing USP XXII specifications grade sterile water for injection from a potable water source which comprises:
   (a) a filtration means adapted to remove particulate impurities from water;
   (b) an adsorption means containing an adsorbent for removing chlorine and dissolved organics;
   (c) a reverse osmosis separation means adapted to remove organics, dissolved solids, microorganisms and pyrogens from water;
   (d) sterile microfiltration means downstream of steps (a), (b) and (c) adapted to remove bacteria from water;
   (e) means for passing the potable grade water through said filtration means, said adsorption means, said reverse osmosis separation means and said sterile filtration means; and
   (f) means for passing heated water periodically through said filtration means, said adsorption means and said reverse osmosis means thereby to flush accumulated pyrogens and to control microorganisms within the said system.

6. The system of claim 5 wherein a deionization means adapted to remove dissolved solids from water is located downstream of said osmosis separation means, means for passing water from said reverse osmosis means through said deionization means and means for periodically passing heated water through said deionization means to flush accumulated pyrogens and to control microorganisms within the said system.

7. The system of claim 5 wherein the potable water is passed sequentially through steps (a), (b), (c) and (d).

8. A system for producing sterile peritoneal dialysis fluid from a potable water source which comprises:
   (a) a filtration means adapted to remove particulate impurities from water;
   (b) an adsorption means containing an adsorbent for removing chlorine and dissolved organics;
   (c) a reverse osmosis separation means adapted to remove organics dissolved solids, microorganisms and pyrogens from water;
   (d) sterile microfiltration means downstream of steps (a), (b), and (c) adapted to remove bacteria from water;
   (e) means for passing the potable grade water through said filtration means, said adsorption means, said reverse osmosis separation means, and said microfiltration means;
   (f) means for proportioning concentrated peritoneal fluids with water exiting said reverse osmosis means and entering said sterile microfiltration means; and
   (g) means for passing heated water periodically through said filtration means, said adsorption means, and said reverse osmosis means thereby to flush accumulated pyrogens and to control microorganisms within the said system.

9. The system of claim 8 wherein the potable water is passed sequentially through steps (a), (b), (c) and (d).

10. The system of claim 8 wherein said heated water also is passed periodically through means (f).

11. A system for producing sterile medical fluids from a potable water source which comprises:
   (a) a filtration means adapted to remove particulate impurities from water;
   (b) an adsorption means containing an adsorbent for removing chlorine and dissolved organics;

(c) a reverse osmosis separation means adapted to remove organics, dissolved solids, microorganisms and pyrogens from water;

(d) sterile microfiltration means downstream of steps (a), (b) and (c) adapted to remove bacteria from water;

(e) means for passing the potable water through said first filtration means, said reverse osmosis separation means and said sterile microfiltration means;

(f) means for proportioning concentrated medicament solutions with water exiting said reverse osmosis means and entering said sterile microfiltration means; and (g) means for passing heated water periodically through said filtration means, said adsorption means and said reverse osmosis means thereby to flush accumulated pyrogens and to control microorganisms within the said system.

12. The system of claim 11 wherein a deionization means adapted to remove dissolved solids from water is located downstream of said reverse osmosis separation means, said means for proportioning being adapted to dispense said medicament with water exiting from said deionization means, means for passing water from said reverse osmosis means through said deionization means and means for periodically passing heated water through said deionization means to flush accumulated pyrogens and to control microorganisms within the said system.

13. The system of claim 11 wherein the potable water is passed sequentially through steps (a), (b), (c) and (d).

14. The system of claim 11 wherein said heated water also is passed periodically through step (f).

15. The system of any one of claims 1, 3, 5, 6, 8, 11 or 12 wherein means (c) is upstream of means (b).

* * * * *